US012616691B2

(12) United States Patent
Philips et al.

(10) Patent No.: US 12,616,691 B2
(45) **Date of Patent: *May 5, 2026**

(54) USE OF FATTY ACID OXIDATION INHIBITORS AS ANTIMICROBIALS

(71) Applicants: Washington University in St. Louis, St. Louis, MO (US); New York University, New York, NY (US)

(72) Inventors: Jennifer A. Philips, St. Louis, MO (US); Kathryn Moore, New York, NY (US); Pallavi Chandra, St. Louis, MO (US); Mireille Ouimet, New York, NY (US)

(73) Assignees: Washington University in St. Louis, St. Louis, MO (US); New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/338,717

(22) Filed: Jun. 21, 2023

(65) Prior Publication Data

US 2024/0000774 A1 Jan. 4, 2024

Related U.S. Application Data

(63) Continuation of application No. 16/979,443, filed as application No. PCT/US2019/022457 on Mar. 15, 2019, now Pat. No. 11,717,519.

(60) Provisional application No. 62/644,105, filed on Mar. 16, 2018.

(51) Int. Cl.

| | |
|---|---|
| ***A61K 31/495*** | (2006.01) |
| ***A61K 31/155*** | (2006.01) |
| ***A61K 31/198*** | (2006.01) |
| ***A61K 31/336*** | (2006.01) |
| ***A61K 31/365*** | (2006.01) |
| ***A61K 31/4453*** | (2006.01) |
| ***A61K 45/06*** | (2006.01) |

(52) U.S. Cl.

CPC .......... *A61K 31/495* (2013.01); *A61K 31/198* (2013.01); *A61K 31/336* (2013.01); *A61K 31/365* (2013.01); *A61K 31/4453* (2013.01); *A61K 31/155* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 7,445,794 | B1 | 11/2008 | Newell et al. | |
| 9,655,958 | B2 | 5/2017 | Coler et al. | |
| 11,717,519 | B2 * | 8/2023 | Philips | A61K 31/336 514/252.12 |
| 2003/0072800 | A1 | 4/2003 | Singh et al. | |
| 2007/0148689 | A1 | 6/2007 | Leishman | |
| 2010/0137192 | A1 | 6/2010 | Shapiro | |
| 2015/0258047 | A1 | 9/2015 | Raqib et al. | |

OTHER PUBLICATIONS

Palanisamy et al. Uptake and Accumulation of Oxidized Low-Density Lipoprotein during Mycobacterium tuberculosis Infection in Guinea Pigs. PLOS ONE. Published 2012. (Year: 2012).*

Oberley-Deegan et al. An oxidative environment promotes growth of Mycobacterium abscessus. Free Radical Biology & Medicine. Published 2010. (Year: 2010).*

Evans et al. Amoxicillin Clavulanate. NIH National Library of Medicine. Published 2023. Retrieved from the Internet on Apr. 12, 2024, https://www.ncbi.nlm.nih.gov/books/NBK538164/. (Year: 2023).*

Singhal et al. Metformin as adjunct antituberculosis therapy, Sc. Translational Med 6, published 2014, pp. 263ra159.

Tselepis et al., Trimetazidine Protects Low-Density Lipoproteins From Oxidation and Cultured Cells Exposed to H2O2 From DNA Damage; Free Radical Biology & Medicine, 2001, vol. 30, No. 12, pp. 1357-1364; (PII. S0891-5849 01)00537-8.

Wadhwa et al.. Steady State Concentration. [Updated Mar. 9, 2022]. In: StatPearls [Internet]. Treasure Island (FL): StatPearls Publishing; Jan. 2022—. Available from: https://www.ncbi.nlm.nih.gov/books/N BK553132/?report=classic (Year: 2022).

* cited by examiner

*Primary Examiner* — James H Alstrum-Acevedo
*Assistant Examiner* — Lauren Wells
(74) *Attorney, Agent, or Firm* — Stinson LLP

(57) ABSTRACT

Methods of using small molecule inhibitors of fatty acid oxidation (FAO) as antimicrobials against intracellular Mycobacteria are disclosed. FAO inhibitors including etomoxir, trimetazidine, oxfenicine perhexeline and/or can be used alone, or in combination with known as antimycobacterial agents against intracellular Mycobacteria.

13 Claims, 22 Drawing Sheets

A. Etomoxir

Ethyl 2-[6-(4-chlorophenoxy) hexyl]oxirane-2-carboxylate

B. Trimetazidine

1-(2,3,4 trimethoxybenzyl)-piperazine dihydrochloride

USE OF FATTY ACID OXIDATION INHIBITORS AS ANTIMICROBIALS

CROSS REFERENCE TO RELATED APPLICATIONS

This application is a continuation of U.S. application Ser. No. 16/979,443, filed on Sep. 8, 2020, which is a U.S. National Phase Application of PCT/US2019/022457 (published as WO 2019/178472), filed on Mar. 15, 2019, which claims priority to U.S. Provisional Application Ser. No. 62/644,105, filed on Mar. 16, 2018, the disclosures of which are hereby incorporated by reference herein in their entireties.

STATEMENT OF GOVERNMENT SUPPORT

This invention was made with government support under AI105298, AI087682, HL108182, HL119047 and AI128427 awarded by the National Institutes of Health. The government has certain rights in the invention.

BACKGROUND OF THE DISCLOSURE

The present disclosure relates generally to the use of small molecule inhibitors of fatty acid oxidation (FAO) as antimicrobials. Particularly, the present disclosure is directed to the use of etomoxir, trimetazidine and/or perhexeline as antimicrobials against intracellular Mycobacteria.

*Mycobacterium tuberculosis* (Mtb) complex causes one of the world's deadliest infections. Particularly, worldwide, there are more than 10 million new cases of tuberculosis annually, resulting in 1.8 million deaths. Mtb survives within macrophages by preventing its own delivery to the degradative, phagolysosomal compartment. Particularly, Mtb induces host microRNA-33 (miR-33), which promotes the intracellular survival of Mtb by inhibiting autophagy and reprograming host lipid metabolism in Mtb-infected macrophages. Autophagy promotes degradation of intracellular bacteria through autophagosomes that deliver bacteria to lysosomes, a process termed xenophagy. Xenophagy does not effectively clear Mtb unless it is activated pharmacologically or by pro-inflammatory cytokines.

While treatments have been developed, Mtb has responded by morphing into multidrug-resistant tuberculosis (MDR-TB), which is resistant to first line anti-TB drugs (e.g., isoniazid and rifampin). Mtb has further developed into extensively drug-resistant tuberculosis (XDR-TB). XDR-TB is caused by bacteria that are resistant to first- and second-line anti-TB drugs, and threatens a global epidemic. Particularly, MDR-TB is an increasing problem, with more than 500,000 cases in 2015, and XDR-TB is found in over 100 countries. Further, the treatment courses are long, complicated, and toxic.

*Mycobacterium abscessus* complex is a group of multi-drug-resistant nontuberculous species. Nontuberculous species can cause pulmonary disease resembling tuberculosis, skin and soft tissue infections, central nervous system infections, bacteremia, and ocular and other infections. *M. abscessus* complex is difficult to treat because of antimicrobial drug resistance, and is a major problem in patients with Cystic Fibrosis.

Host directed therapeutics (HDTs) may engender less resistance than drugs that directly target bacteria and might modulate immunopathology in a beneficial way. By targeting infected host cells, HDTs might also effectively eradicate slowly growing or non-replicating bacilli, thereby shortening therapy when used in combination with conventional antibiotics. Accordingly, there exists a need for developing HDTs for tuberculosis (TB) and nontuberculous Mycobacteria infections.

BRIEF DESCRIPTION

The present disclosure is generally directed to the use of the FAO inhibitors as antimicrobials against intracellular Mycobacteria infections. FAO inhibitors are particularly useful for treating *Mycobacterium tuberculosis* (Mtb) infections and nontuberculous Mycobacteria infections. In some embodiments, the FAO inhibitors are incorporated into compositions with pharmaceutically acceptable carriers. In some embodiments, the FAO inhibitors are used in combination with other therapeutics, such as other known anti-mycobacterial agents.

In one aspect, the present disclosure is directed to a method of treating Mycobacteria infection in a subject in need thereof, the method comprising administering a fatty acid oxidation (FAO) inhibitor to the subject. In one embodiment, the Mycobacteria is *Mycobacterium tuberculosis* complex. In one embodiment, the Mycobacteria is *Mycobacterium abscessus* complex.

In another aspect, the present disclosure is directed to a method of inhibiting intracellular growth of *Mycobacterium* in a subject in need thereof, the method comprising administering a fatty acid oxidation (FAO) inhibitor to the subject. In one embodiment, the Mycobacteria is *Mycobacterium tuberculosis* complex. In one embodiment, the Mycobacteria is *Mycobacterium abscessus* complex.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 5A depicts WT macrophages and Cpr2 conditional knockout (cKO) mutant cells infected with Mtb. CFU were enumerated 4 and 72 hours post-infection (hpi). FIG. 5B depicts WT and Cpt2−/− cKO macrophages treated with metformin, etomoxir (ETM), trimetazidine (TMZ), or untreated and infected with Mtb. CFU were enumerated 72 hpi.

FIG. 6A depicts representative images showing an increased co-localization of intracellular Mtb with p62 (white arrow in 5 nM TMZ treated). FIG. 6B depicts the quantification of co-localization of intracellular Mtb with p62 in untreated and TMZ treated cells. FIG. 6C is a graph depicting an increase in total p62 puncta per cell upon TMZ treatment. FIG. 6D is a graph depicting H37Rv CFUs in wild type (wt) and Parkin2-deficient (Parkin2KO) macrophages after 72 hours TMZ treatment. Values are mean±SEM, ****p-value=0.0001, calculated using Student's t-test and one-way ANOVA.

FIG. 7C depicts Mtb-infected wild type (wt) and Nox2KO BMDMs at 3 hours post infection and TMZ treatment and in uninfected immortalized BMDMs treated with TMZ for 3 hours with and without mitoTEMPO (FIG. 7D). FIG. 7E depicts quantification of an increase in mitochondrial ROS using MitoSOX staining in uninfected wt BMDMs treated with TMZ for 3 hours. FIG. 7F depicts mitoTEMPO rescue of Mtb CFU in TMZ treated macrophages. Values are mean±SEM, p-values calculated using one way ANOVA. FIGS. 7D and 7E depict box and whisker pilots showing mean and 1-99 percentile values.

FIG. 8A is a graph depicting H37Rv-infected wild type (wt) and Nox2KO BMDMs treated with TMZ (5 nM) and total cell ROS measured at 24 hours post treatment. FIG. 8B shows representative images showing increased co-localization of Mtb (observed in the red channel) and NOX2 (observed in the green channel) in wt BMDMs upon TMZ treatment (DAPI used to stain nuclei). FIG. 8C depicts quantification of Mtb and NOX2. Values are mean±SEM, *p-values calculated using one-way ANOVA and Student's t-test.

FIG. 12C depicts *M. abscessus* CFUs, 48 hpi from BMDMs treated with 5 nM TMZ. Values are mean±SEM, p-values were determined using Student's t-test.

FIG. 13A depicts a Western blot for LC3 in H37Rv-infected BMDMs treated with 500 nM TMZ alone or in combination with bafilomycinA1 for 3 hrs. The band intensity of LC3-II was normalized to $-actin controls and the value is shown in white. FIG. 13B depicts total cell ROS measured in Mtb infected wt (Cre−) and Atg5 KO BMDMs treated with TMZ and mitoTEMPO. ***p-value=0.0001, by one way ANOVA.

FIG. 14 depicts uninfected wt BMDMs treated with 500 nM TMZ for 3 hrs, alone or in combination with ETC inhibitors rotenone and antimycin. Shown here is a plot of mitoSOX signal from ~20-30 cells.

DETAILED DESCRIPTION

Figure 1:
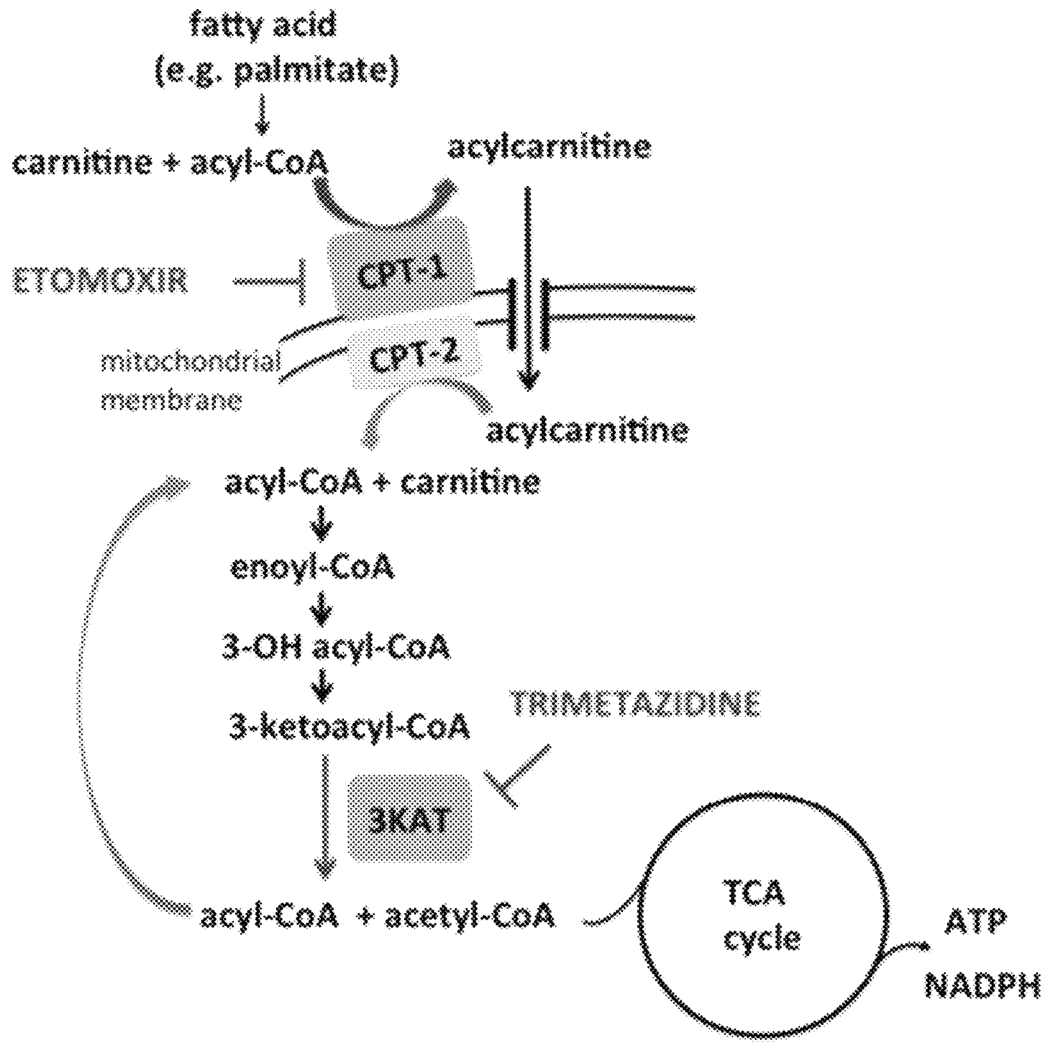
FIG. 1 depicts the carnitine shuttle and FAO. Long chain fatty acids are transported across the plasma membrane and activated to acyl CoA derivatives, which are converted to acylcarnitines by CPT-1 at the outer mitochondrial membrane. Etomoxir and perhexiline inhibit CPT-1. Acylcarnitines are transported across the mitochondrial membrane by a dedicated translocase. In the mitochondria, CPT-2 converts acylcarnitines back to acyl-CoA and carnitine. Acyl-CoA chains then undergo f-oxidation, successively generating acetyl-CoA that enters the TCA cycle. Trimetazidine inhibits long-chain 3-ketoacyl-CoA thiolase, which catalyzes the release of acetyl-CoA from the acyl-CoA chain.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

FAO inhibitors work by shifting metabolism from fatty acids to glucose, resulting in more energy production per oxygen consumed. They also improve coupling between glycolysis and glucose oxidation.

It has been unexpectedly found these small molecule inhibitors of FAO inhibit intracellular growth of Mtb, thereby functioning as effective host directed therapeutics (HDTs) for tuberculosis (TB). While it is known that Mtb utilizes host lipids as a carbon source in vivo, it was surprisingly found herein that host fatty acid catabolism is required for intracellular growth of Mtb. In fact, this is counter to expectations if the bacteria are competing with the host for fatty acid utilization. Further, given the recent observations that Mtb induces the Warburg effect, a shift from fatty acid oxidation to glycolysis, it was surprising that further shifting metabolism away from fatty acid oxidation would be beneficial to the host.

It has also been found that these small molecule inhibitors of FAO inhibit intracellular growth of rapidly growing, non-tuberculous mycobacteria. Rapidly growing, non-tuberculous mycobacteria include, for example, *M. abscessus* complex, *M. fortuitum, M. chelonae*, and other known non-tuberculous mycobacteria. Therefore, these small molecule inhibitors of FAO also function as effective HDTs for rapidly growing, non-tuberculous mycobacteria.

The present disclosure is thus generally directed to the use of FAO inhibitors for treating *Mycobacterium* infection. In some embodiments, the *Mycobacterium* infection is *Mycobacterium tuberculosis* (Mtb) infection. In some embodiments, the FAO inhibitors can be used for treating multi-drug-resistant tuberculosis (MDR-TB), and further even extensively drug-resistant tuberculosis (XDR-TB).

In some embodiments, the *Mycobacterium* infection is *Mycobacterium abscessus* infection (also referred to herein as nontuberculous mycobacteria). *M. abscessus* complex includes *M. abscessus* subsp. *abscessus, M. abscessus* subsp. *massiliense*, and *M. abscessus* subsp. *bolletii*. In some embodiments, the FAO inhibitors can be used for treating respiratory tract infections. The diagnosis of *M. abscessus* complex pulmonary disease can be made by the presence of clinical symptoms; radiographic evidence of lesions compatible with NTM pulmonary disease; appropriate exclusion of other diseases; and positive culture results from at least 2 separate expectorated sputum samples. In some embodiments the *Mycobacterium abscessus* infection is a skin and soft tissue infection (SSTI). SSTI can range from deep tissue infections to localized skin infections. *M. abscessus* complex skin infection can present as cutaneous nodules (usually tender), erythematous papules/pustules, and papular eruptions or abscesses. In some embodiments the *Mycobacterium abscessus* infection is a central nervous system infection occurring as meningitis and cerebral abscessess. In some embodiments the *Mycobacterium abscessus* infection is a bacteremia and disseminated infection. In some embodiments the *Mycobacterium abscessus* infection is an ocular infection such as keratitis, endophthalmitis, scleritis, and other tissues of the ocular area. In some embodiments, the *M. abscessus* (or other rapidly growing mycobacteria) infection is related to a post-surgical and/or prosthetic device infection.

Figure 2A:
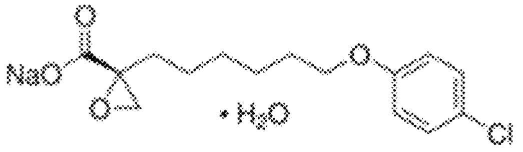
FIGS. 2A & 2B depict the structures of etomoxir and trimetazidine.
Figure 2B:
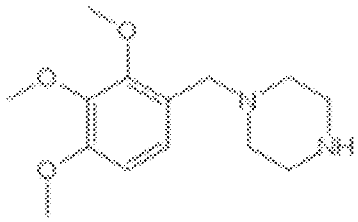

The FAO inhibitors can include etomoxir, trimetazidine, oxfenicine, perhexeline and mildronate. More particularly, the small molecule inhibitors, etomoxir (ethyl 2-[6-(4-chlorophenoxy)hexyl]oxirane-2-carboxylate) and trimetazidine (1-(2,3,4-trimethoxybenzyl)piperazine), inhibit distinct steps in the β-oxidation of fatty acids (FIGS. 1 and 2A & 2B). Etomoxir inhibits carnitine palmitoyltransferase 1 (CPT-1), which is required for the entry of long chain fatty acids into the mitochondrial matrix as part of the carnitine shuttle, a rate-limiting step in FAO. The acylcarnitine generated by CPT-1 is transported into the mitochondrial matrix, where CPT-2 catalyzes the reverse reaction, regenerating the acyl-CoA ester. The acyl-CoA ester is then subject to enzymatic reactions that culminate in the removal of one acetyl-CoA group per cycle. 3-Ketoacyl-CoA thiolase (3-KAT), the target of trimetazidine, catalyzes the terminal reaction that liberates the acetyl-CoA, which can then enter the tricarboxylic acid (TCA) cycle. Perhexeline (2-(2,2-dicyclohexylethyl)piperidine) is thought to act by inhibiting mitochondrial carnitine palmitoyltransferase-1. Oxfenicine ((2S)-2-amino-2-(4-hydroxyphenyl)acetic acid) is an inhibitor of fatty acid oxidation that acts at the level of CPT-1. Meldonium (2-(2-Carboxylato-ethyl)-1,1,1-trimethylhydrazinium) is a substrate for gamma-butyrobetaine dioxygenase and binds to the substrate pocket of γ-butyrobetaine hydroxylase and thereby acts as an alternative substrate, and therefore a competitive inhibitor.

Suitable dosages of the FAO inhibitors for use in the methods of the present disclosure will depend upon a number of factors including, for example, age and weight of an individual, drug-resistant tuberculosis, severity of the tuberculosis, specific inhibitor to be used, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result. In some embodiments, the inhibitor is etomoxir, and etomoxir is administered at a dosage such to achieve concentrations of from about 5 μM to about 100 μM, including from about 10 μM to about 50 μM, including about 25 μM to about 50 μM and including about 25 μM. In other embodiments, the inhibitor is trimetazidine, and trimetazidine is administered at a dosage such to achieve concentrations of from about 1 nM to about 1000 nM, including from about 1 nM to about 500 nM, and including about 50 nM. Trimetazindine can also be administered at a dosage ranging from about 16 mg/kg/day to about 250 mg/kg/day. In other embodiments, the inhibitor is oxfenicine and is administered at a dosage such to achieve concentrations of from about 1 nM to about 5000 nM, including from about 1 nM to about 5000 nM, and including about 50 nM. In other embodiments, the inhibitor is perhexiline and is administered at a dosage such to achieve concentrations of from about 1 nM to about 5000 nM, including from about 1 nM to about 5000 nM, and including about 50 nM. In other embodiments, the inhibitor is Meldonium (MILDRONATE) is administered at a dosage ranging from about 500 mg per day to about 2 g per day.

In some embodiments, the inhibitors are administered in the form of a composition including the inhibitor and at least one pharmaceutically acceptable carrier. Suitable pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (i.e., etomoxir, trimetazidine and/or perhexeline) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating *Mycobacterium* infection. For example, in one embodiment, the FAO inhibitors can be administered with additional antimycobacterial agents. One particularly suitable additional antimycobacterial agents may be, for example, isoniazid (INH), rifampin, ethambutol, pyrazinamide, streptomycin, amikacin, capreomycin, bedaquiline, delamanid, fluoroquinolones (such as moxifloxacin), linezolid, ethionamide, prothionamide, cycloserine, terizidone, p-aminosalicylic acid, clofazamine, amoxicillin/clavulanate, thioacetozone, clarithromycin, and imipenem.

In another embodiment, the FAO inhibitors can be administered with additional agents that alter host metabolism, autophagy, cell death pathways, inflammation, and/or signaling pathways. Particularly suitable additional agents may be, for example, metformin, statins, valproic acid, carbamezapine, vorinostat, phenylbutyrate, rapamycin, imatinib, desipramine, alisporivir, COX inhibitors (such as aspirin, ibuprofen), zileuton, bestatin, sildenafin, and pentyoxyfylline.

The pharmaceutical compositions including etomoxir, trimetazidine, perhexeline and/or pharmaceutical carriers used in the methods of the present disclosure can be administered to a subset of individuals in need. As used herein, an "individual in need" refers to an individual at risk for or having a *Mycobacterium* infection such as *Mycobacterium tuberculosis* (Mtb), and in particular, multidrug-resistant tuberculosis (MDR-TB) and/or extensively drug-resistant tuberculosis (XDR-TB) and nontuberculous mycobacteria. Additionally, an "individual in need" is also used herein to refer to an individual at risk for or diagnosed by a medical professional as having Mtb and nontuberculous mycobacteria. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, the relationship between FAO inhibition and intracellular Mtb growth was analyzed.

Figure 3A:
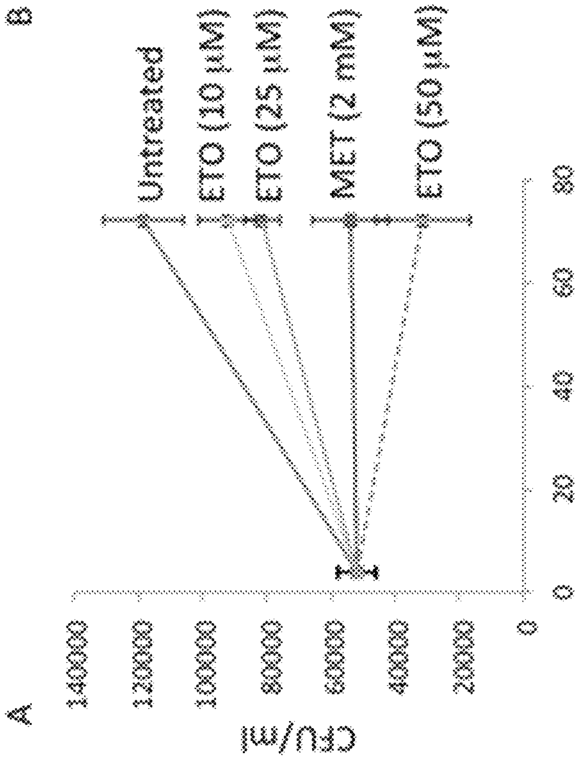
FIGS. 3A-3C show that etomoxir, trimetazidine, metformin and oxfenicine (OXF) inhibit intracellular survival of Mtb. Bone marrow-derived macrophages (BMDMs) were infected with Mtb (strain H37Rv). Extracellular bacteria were removed 4 hpi, and BMDMs were treated with vehicle control or etomoxir (ETO) and metformin (MET) (FIG. 3A), trimetazidine (TMZ) (FIG. 3B), or metformin (MET) and oxfenicine (FIG. 3C) at indicated concentrations for 72 hours and colony forming unites (CFU) were enumerated. Data are from one representative experiment and show mean+/−SD from 5 replicates; $p<0.05$, Student's t-test for all drug treated conditions compared to control. Higher doses of TMZ did not result in an increased antimicrobial effect, and there was no significant difference between TMZ doses.

Mtb-infected macrophages were treated with 10, 25, or 50 μM etomoxir, concentrations that inhibit macrophage FAO. Mtb viability was assayed 72 hours post-infection (hpi) by plating for colony forming units (CFU; FIG. 3A). Etomoxir exhibited a dose dependent inhibition of Mtb. Etomoxir did not directly prevent Mtb growth, even at ten times the dose that inhibited intracellular Mtb (Table 1). The absence of direct antibacterial activity suggests that etomoxir acts on a host target.

TABLE 1

| MIC on Mtb (H37Rv) in liquid | |
|---|---|
| Drug | MIC |
| Etomoxir | >250 μM |
| Perhexiline | >100 μM |
| Oxfenicine | >140 mM |
| Trimetazidine | 1 mM |
| Metformin | >15 mM |
| INH | <0.3 μM |

Figure 3B:
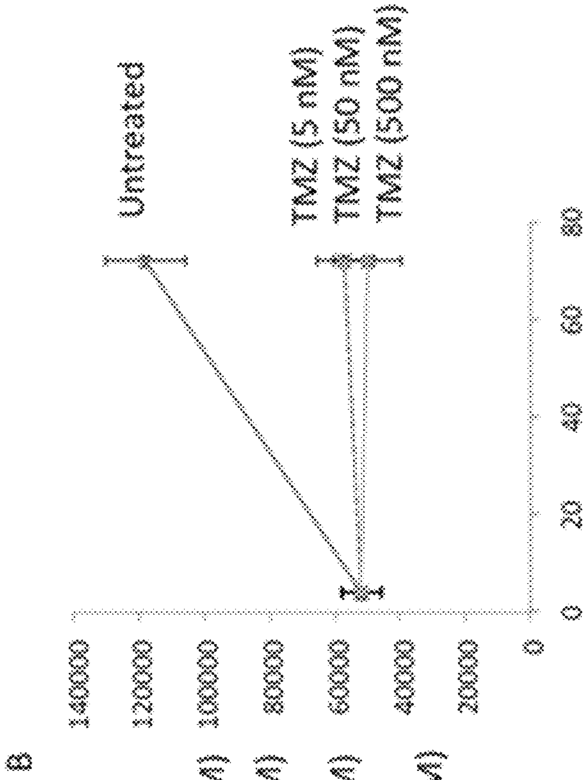
Figure 3C:
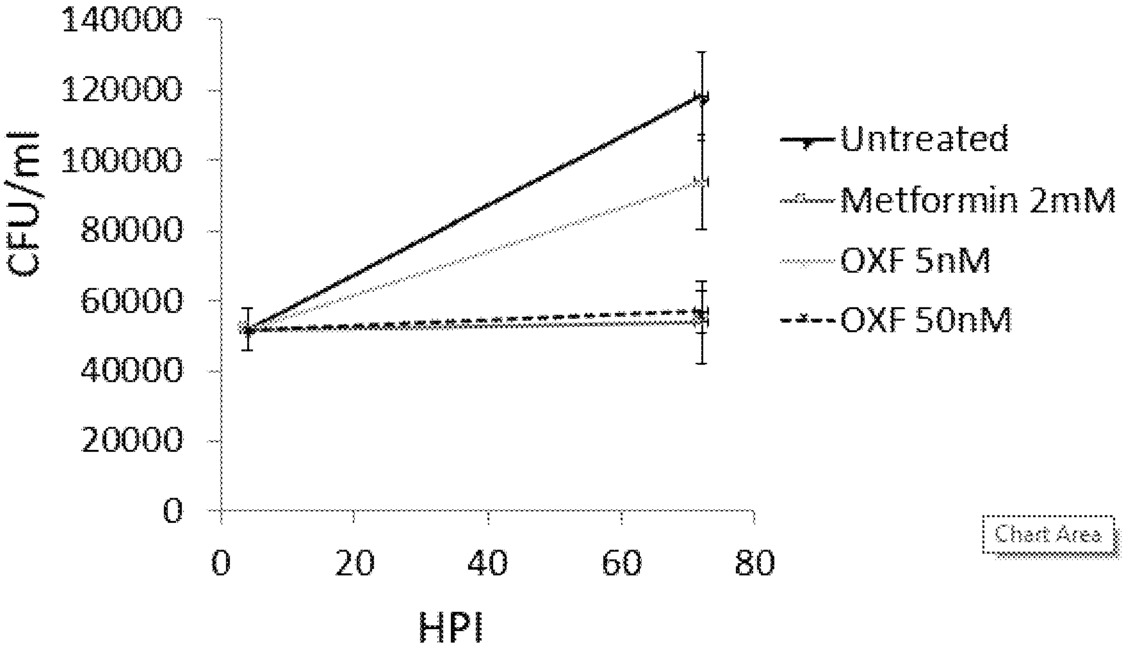
Figure 4A:
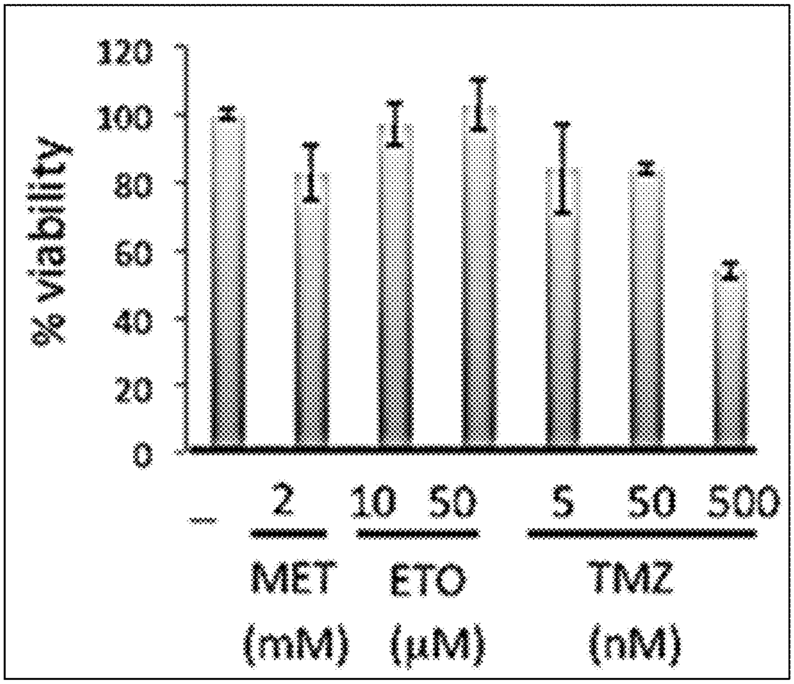
FIG. 4A depicts the effect of metformin, etomoxir, and trimetazidine on macrophage viability.
Figure 4B:
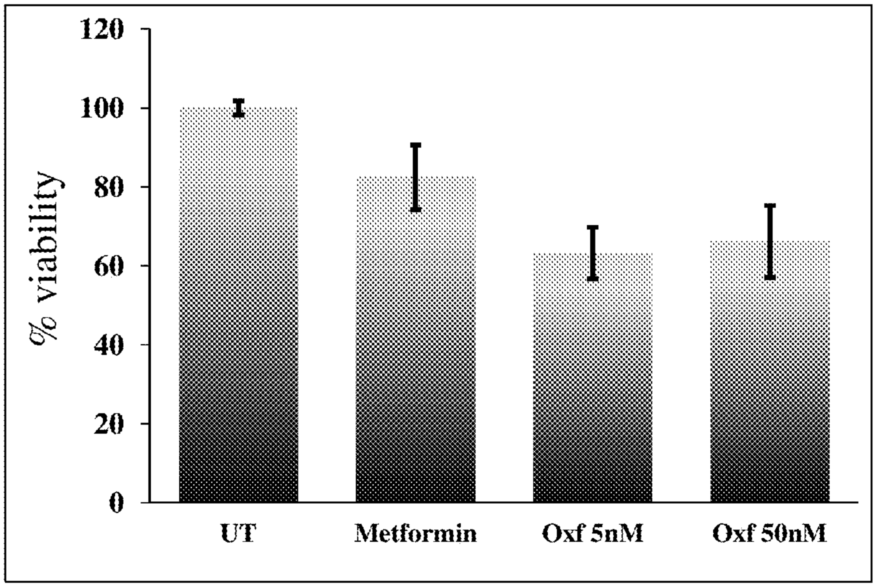
FIG. 4B depicts the effect of metformin and oxfenicine on macrophage viability. BMDMs were treated with the indicated concentration of compound for 72 hours, and viability was assessed using the cellular dye, calcein-AM, and normalized to untreated controls (--). Data are mean+/−SD.

To determine whether antibacterial activity was specific for etomoxir and CPT-1 inhibition, the antimicrobial activity of trimetazidine (TMZ), which inhibits FAO by blocking long-chain 3-KAT, was then determined. Remarkably, it was found that concentrations as low as 5 nM inhibited intracellular Mtb growth (FIG. 3B). The ability to inhibit Mtb growth at nM concentrations is consistent with an on-target effect, as TMZ inhibits long-chain 3-KAT activity in rat heart mitochondria at doses between about 10 nM and about 100 nM ($IC_{50}$~75 nM). Importantly, plasma concentrations of TMZ in patients treated for angina (60 mg/day) are 70-100 nM, in line with the ability of TMZ to inhibit FAO in intact hearts at 100 nM. The antimicrobial activity was not related to macrophage toxicity (FIG. 4). BMDMs were treated with the indicated concentration of compound for 72 hours, and viability was assessed using the cellular dye, calcein-AM, and normalized to untreated controls (--).

Importantly, the antimicrobial activities of etomoxir and trimetazidine compared favorably to 13 autophagy-activating drugs and other host-directed compounds under investigation. For example, comparable antimicrobial activity of metformin requires millimolar concentrations (FIG. 3A). This data suggest that intracellular growth of Mtb depends upon FAO by the infected macrophage.

Example 2

In this example, the minimal inhibitory concentration (MIC) of the FAO inhibitors, etomoxir and trimetazidine on mycobacteria inside of macrophages was determined and compared to their inhibition of FAO.

If CPT-1 and 3-KAT are the relevant antimicrobial targets, respectively, concordance in the potency of the compounds is anticipated in the assays. Previous studies found that FAO is blocked in murine and human monocyte-derived macrophages by 10-25 μM etomoxir, concentrations that exhibit antimycobacterial activity. The antimycobacterial MIC of trimetazidine was 5 nM in murine macrophages. The MIC of TMZ against Mtb in human THP1 cells was approximately 50 nm. The ability to inhibit Mtb growth at nM concentrations is consistent with an on-target effect, as TMZ inhibits long-chain 3-KAT activity in rat heart mitochondria at doses between about 10 nM and about 100 nM ($IC_{50}$~75 nM).

The antimicrobial activity and FAO inhibition was analyzed for cellular toxicity. BMDMs were treated with the indicated concentration of compound for 72 hours, and viability was assessed using the cellular dye, calcein-AM, and normalized to untreated controls (--). As shown in FIG. 4, it is unlikely that host cell death is responsible for the observed antimicrobial effects.

Example 3

In this Example, the antibacterial activity of FAO inhibitors and its dependence upon known host targets was evaluated.

There are three isoforms of Cpt-1. Cpt-1a is expressed in most tissues, whereas Cpt-1b and Cpt-1c are restricted to muscle and brain, respectively. 3-KAT is a component of the mitochondrial trifunctional protein. The β-subunit (HADHB) catalyzes the thiolase activity.

Figure 5B:
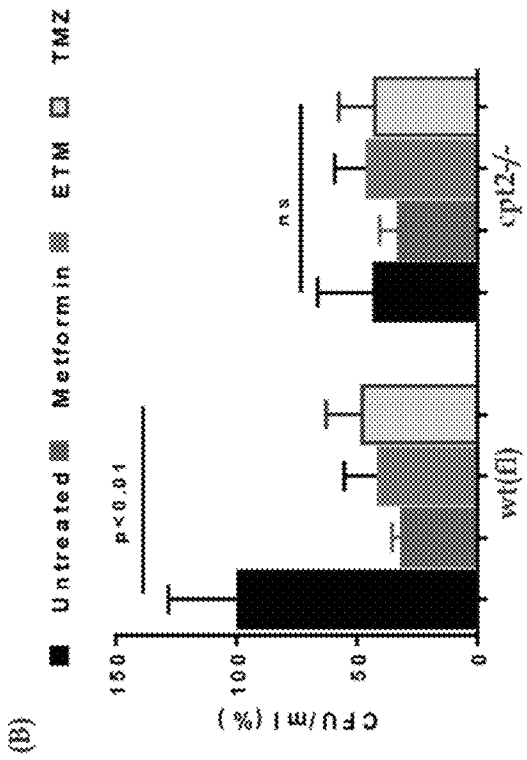
FIGS. 5A & 5B depict that Cpt2 promotes intracellular growth of Mtb and is required for activity of FAO inhibitors.
Figure 5A:
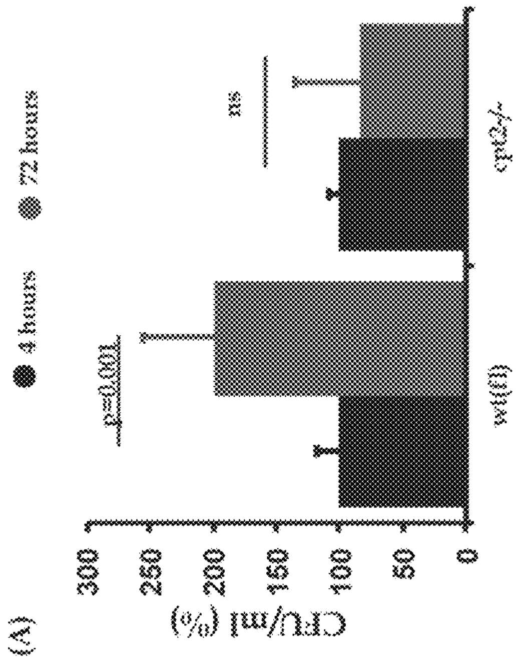

Bone marrow stem cells from Cpt-$2^{flox/flox}$ LysM-Cre+ mice were obtained. Although Cpt-2 is not the direct target of either etomoxir or trimetazidine, it is required in the same pathway (FIG. 1). Accordingly, the activity of etomoxir and trimetazidine was evaluated in Cpt-2 mutant cells as compared to wild type (wt) cells using the assays described above. The activity of etomoxir and trimetazidine was compared to the activity of metformin in these cells. Results are shown in FIGS. 5A & 5B. The antimicrobial activity of etomoxir and trimetazidine depended upon Cpt2, consistent with their antimicrobial activity being due to inhibition of fatty acid oxidation.

Example 4

In this Example, whether FAO inhibitors activate autophagy was determined.

Wild type BMDMs were infected with H37Rv expressing DsRed at MOI 1:5 for 4 hours. After bacterial uptake, the culture medium was supplemented with TMZ (5 nm). At 24 hours post infection (hpi), samples were fixed and immunostained with p62 (green). Alternatively, bacterial numbers were enumerated by CFU at 3 days post infection (dpi). For IF, images were captured using a confocal microscope equipped with a 60× oil immersion objective lens. To quantify co-localation of Mtb and autophagosomes each bacteria was converted to a region of interest (ROI) and the mean fluorescence intensity of the p62 signal was measured. To assess autophagy induction, the total p62 puncta per cell in shapes that were untreated or treated with TMZ. IFN-γ, which activates autophagy, was used as a positive control.

Figure 6A:
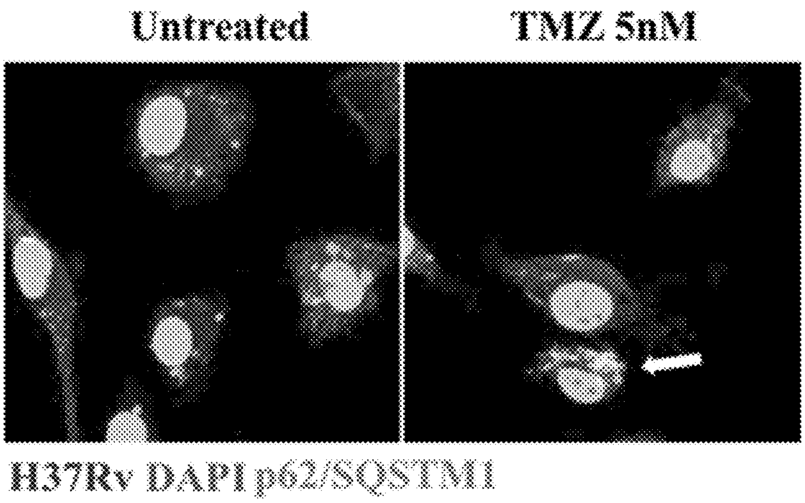
FIGS. 6A-6D depict TMZ induction of autophagy in host macrophages.
Figure 6B:
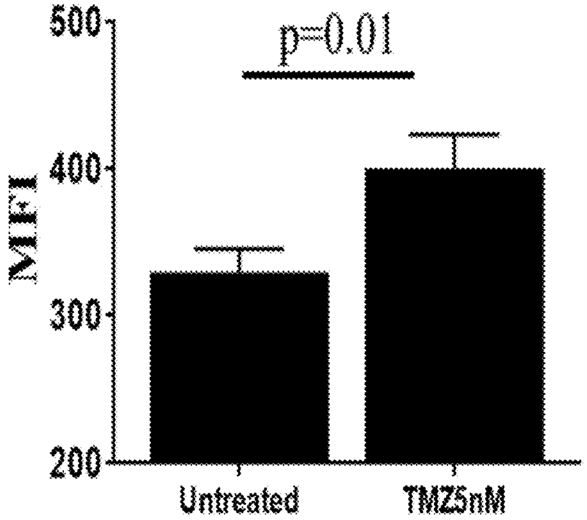
Figure 6C:
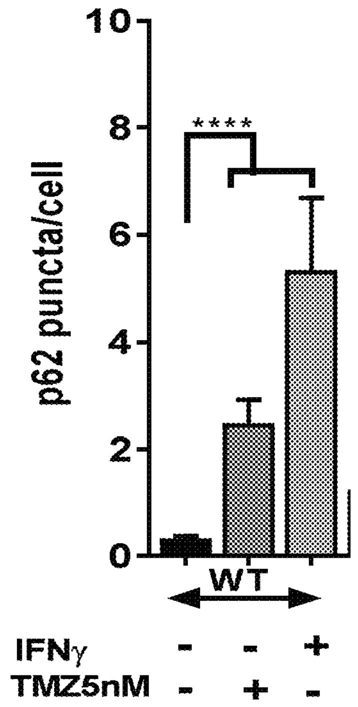
Figure 6D:
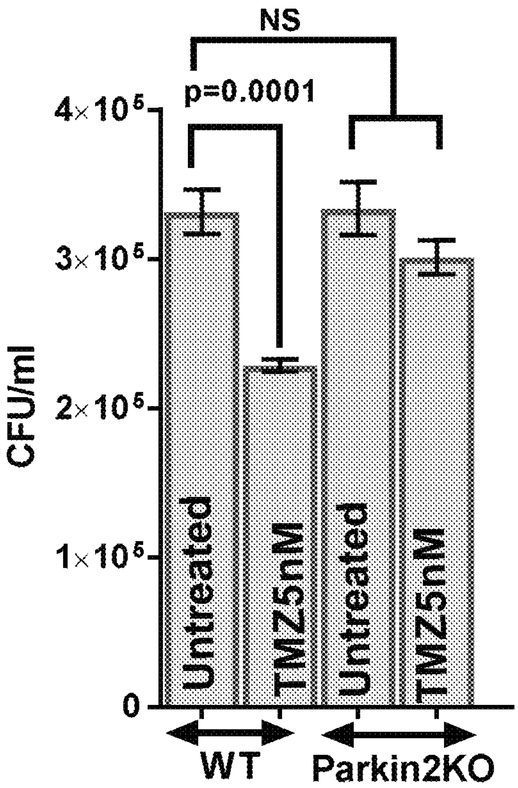

As shown in FIGS. 6A and 6B, co-localization of H37R and p62 was increased by TMZ treatment. Additionally, TMZ treatment significantly increased the total number of p62 puncta in macrophages (FIG. 6C). A deficiency of Parkin2 rescued Mtb from TMZ treatment (FIG. 6D).

These results indicated that FAO inhibition induces xenophagy.

Example 5

In this Example, whether FAO inhibition promotes oxidative stress to restrict Mtb growth was determined.

Total cellular ROS levels were compared in FAO inhibitor-treated and untreated samples using CellRox (Molecular Probes) staining. Macrophages were infected as previously described and co-localization of Mth with subunits of the NADPH oxidase ($p40^{phox}$ and $gp91^{phox}$/NOX2) were monitored in FAO inhibitor-treated and untreated samples. To determine whether FAO inhibition induced oxidative stress in the host, uninfected RAW 264.7 cells were treated with TMZ at 5 nM and 500 nM and ETM at 50 μM and total cellular ROS was determined at 1, 3, and 24 hours post-treatment using CellRox dye. In parallel, tert-butyl hydroperoxide (0.5 mM tBHP) was used as a positive control. The samples were imaged using confocal microscopy and the fluorescence intensity of each cell was quantified.

Figure 7A:
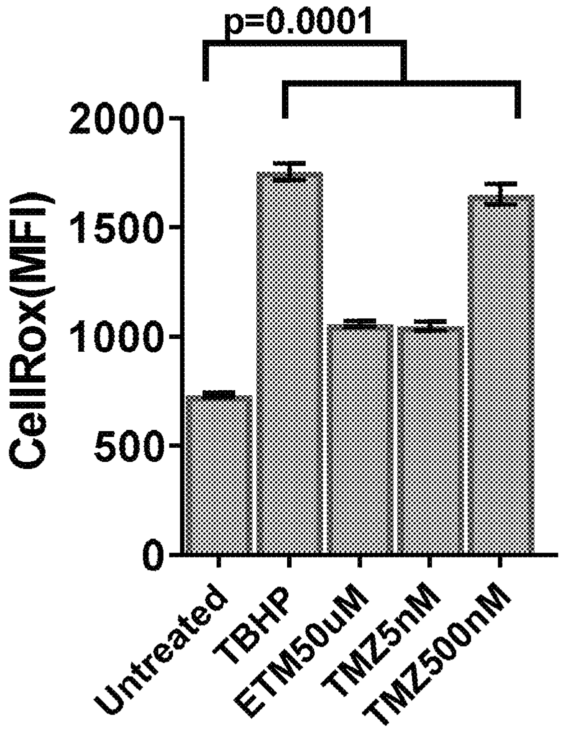
FIGS. 7A-7F depict FAO inhibition promotes an early mitochondrial ROS production. Total cell ROS was measured in uninflected RAW 264.7 macrophages at 3 hours (FIG. 7A) and 24 hours (FIG. 7B) post treatment with FAO inhibitors.
Figure 7B:
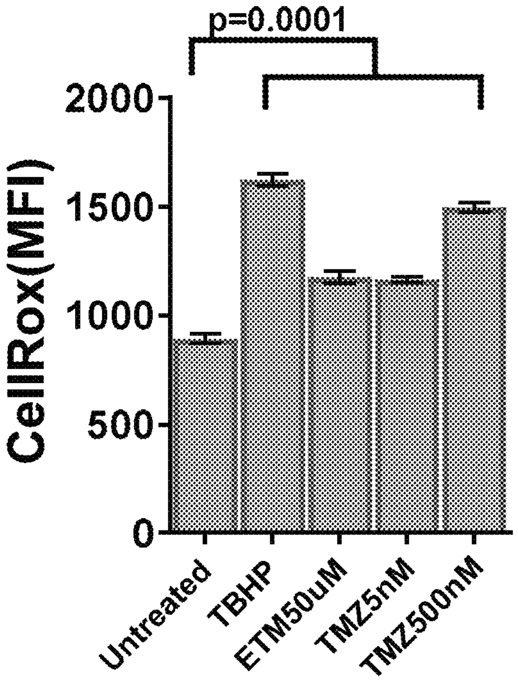
Figure 7C:
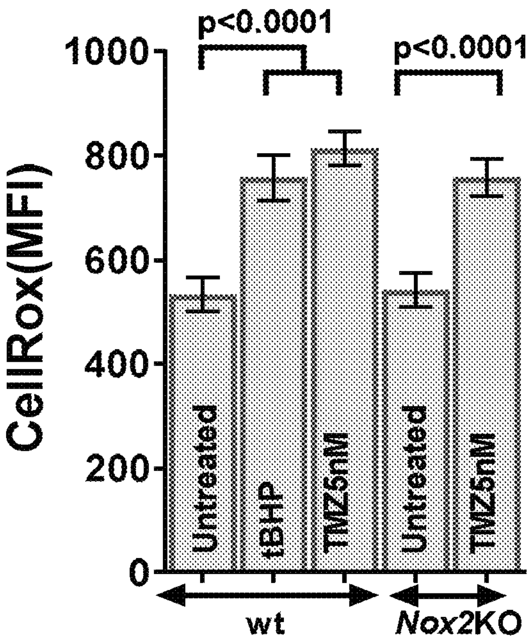

As shown in FIGS. 7A and 7B, FAO inhibition significantly increased ROS production in macrophages as early as 3 hours post treatment. This result was validated in Mtb infected BMDMs as well (FIG. 7C). ROS production was compared in wild type (wt) and Nox2 knockout (KO) BMDMs upon FAO inhibition.

Figure 7D:
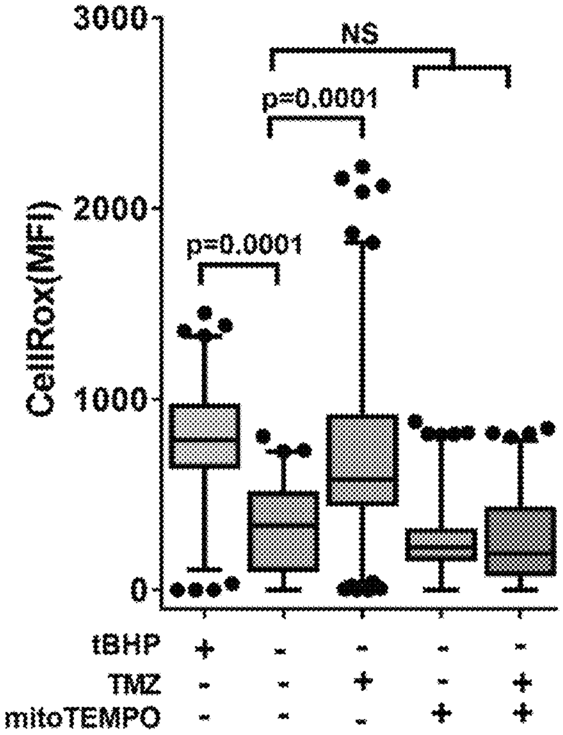
Figure 7E:
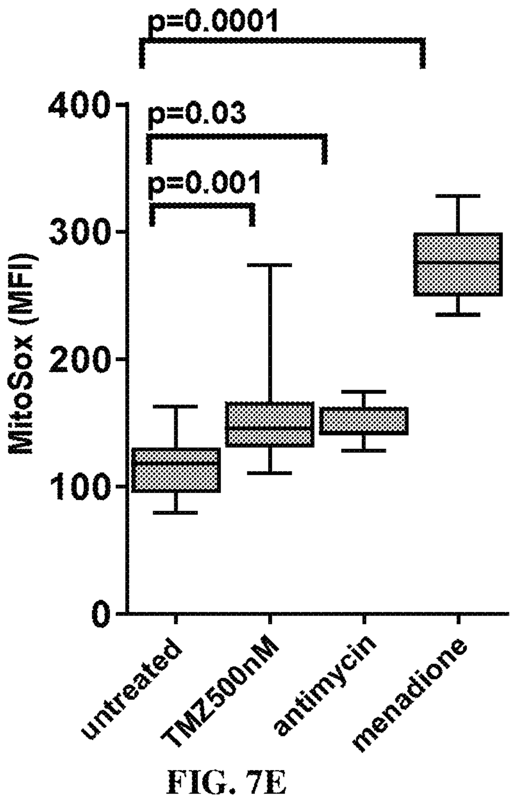
Figure 7F:
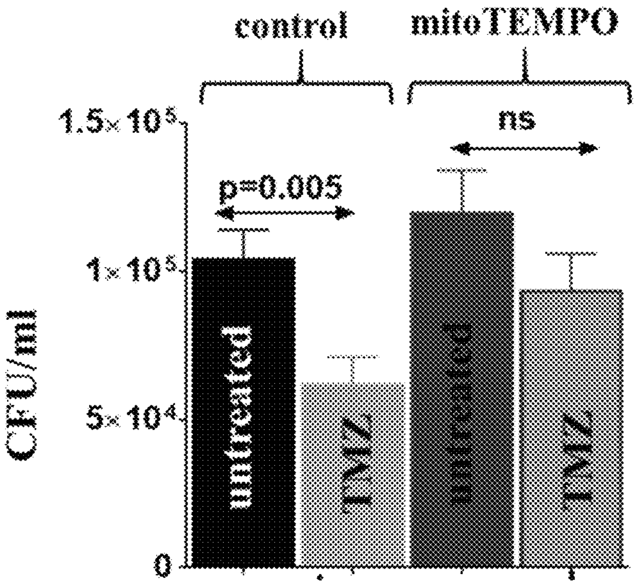

The results indicated that the early ROS burst induced by TMZ was not generated by the NADPH oxidase. It was reasoned that an alternate source of ROS at the 3 hour time point could be the host mitochondria. To test this, 10 μM mitoTEMPO (mitochondrial ROS scavenger) was added to TMZ treated samples. ROS production was abolished upon TMZ treatment (FIG. 7D). These results were further confirmed by directly measuring mitochondrial ROS using MitoSOX dye (FIG. 7E). Next, the anti-mycobacterial activity of TMZ was tested in the presence of mitoTEMPO. Mtb-infected wild type BMDMs were treated with 50 nM TMZ with or without mitoTEMPO and Mtb CFUs were estimated after 120 hours. As shown in FIG. 7F, TMZ lost its anti-mycobacterial activity in the absence of mitochondrial ROS.

Figure 8A:
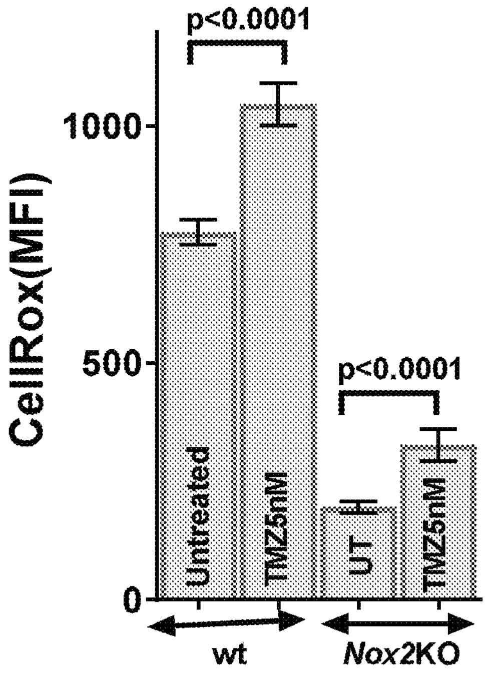
FIGS. 8A-8C depict TMZ requirement of NADPH oxidase for its anti-mycobacterial activity.
Figure 8B:
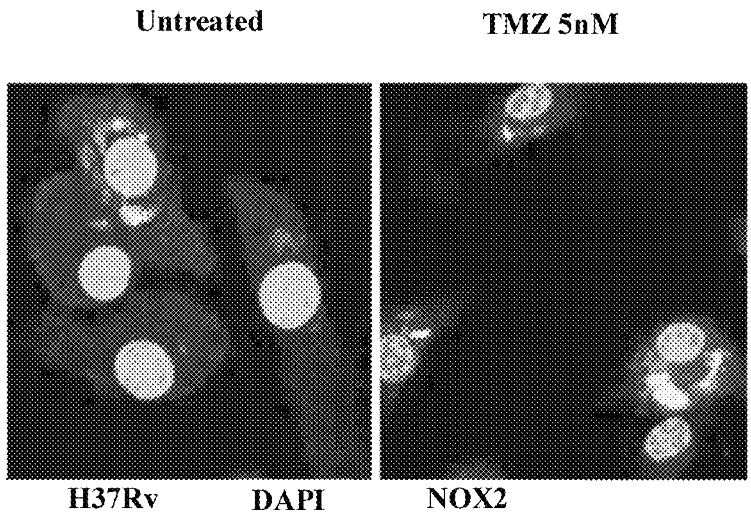
Figure 8C:
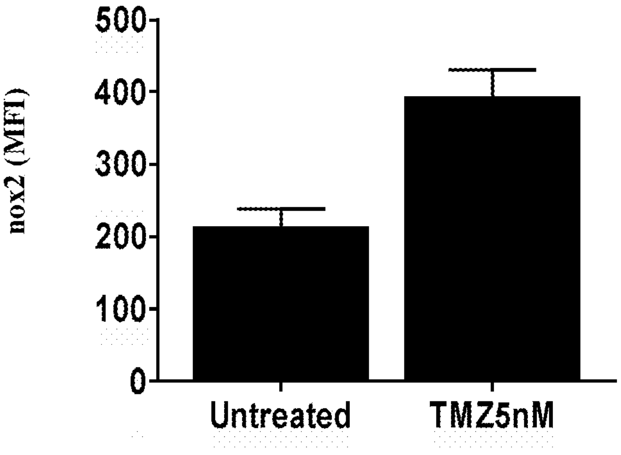

The data obtained from early time points did not show a dependence of TMZ activity on NADPH oxidase. Thus, later time points were tested. Total cell ROS was estimated in Mtb-infected wild type and Nox2 KO BMDMs after 24 hours of TMZ treatment (FIG. 8A). TMZ induced ROS in wild type BMDMs. Nox2 KO BMDMs were deficient in overall ROS production as compared to wild type macrophages. TMZ was able to produce a significant increase in ROS in Nox2 KO BMDMs, however, which could be attributed to mitochondria. The recruitment of NADPH oxidase subunits $gp91^{phox}$/NOX2 and $p40^{phox}$ was monitored on mycobacterial phagosomes upon TMZ treatment. Staining shows co-localization of Mtb and NOX2 (FIG. 8B). Mtb and NOX2 were increased in samples treated with TMZ after 24 hours (FIG. 8C).

Figure 13A:
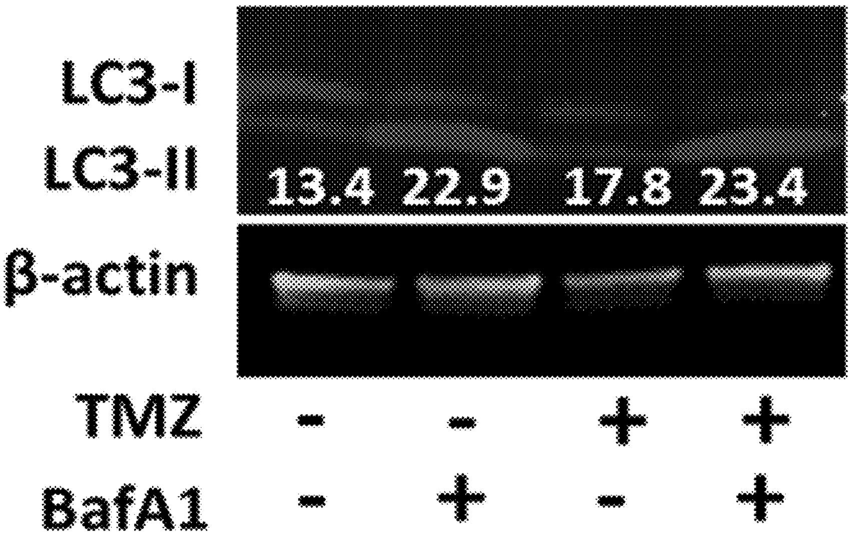
FIGS. 13A & 13B depict early mitochondrial ROS production by TMZ does not depend on autophagy.
Figure 13B:
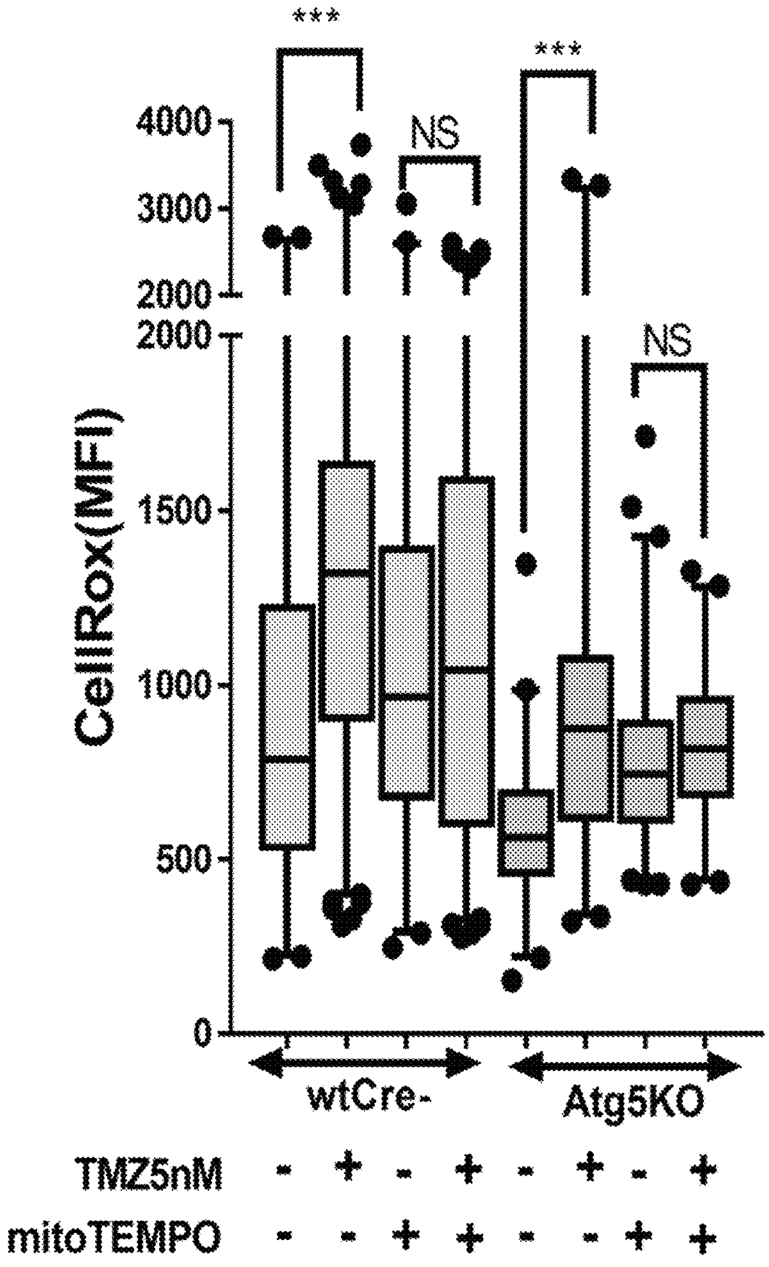

To determine whether autophagy was also induced in the same time frame, BMDMs were infected with H37Rv at MOI 1:5 and treated with 500 nM TMZ for 3 hours. Autophagy flux was monitored in sample cell lysates by comparing LC3 levels with and without bafilomycin A1 (BafA1) treatment. No changes in autophagy flux were observed after 3 hour TMZ treatment (FIG. 13A). Further, total cell ROS production after 3 hour TMZ treatment was compared in Mtb infected wt and Atg5 KO BMDMs. Although total cellular ROS was reduced in autophagy-deficient macrophages as compared to wt cells, TMZ treatment increased ROS signal even in autophagy deficient macrophages (FIG. 13B). Moreover, mitoTEMPO which specifically scavenges mitochondrial ROS, abolished the enhanced cellular ROS production elicited by TMZ. Thus, TMZ induced an early mitochondrial ROS burst which preceded, and was not dependent upon autophagy induction.

These results indicated that FAO inhibition promoted two kinds of responses that generate ROS to restrict Mtb growth. In particular, an early mitochondrial ROS burst was observed and dependence of anti-mycobacterial activity of TMZ on NADPH oxidase was observed, which its role became more evident during later time points.

Example 6

In this Example, whether FAO inhibition alters inflammatory responses in Mtb infected macrophages was determined.

Oxygen consumption rate (OCR) and extracellular acidification rate (ECAR) was measured using SeaHorse Analyzers in uninfected wild type and FAO-deficient carnitine palmitoyltransferase 2 KO (Cpt2 cKO) BMDMs treated with 5 nM TMZ. Additionally, whether FAO inhibitors promoted pro-inflammatory signaling was tested. Wild type macrophages were infected with H37Rv and treated with 5 nM TMZ for 24 and 72 hpi. Following filter sterilization, sample supernatants were examined for pro-inflammatory cytokines including, IL-1β, IL-6, TNF-α, and the anti-inflammatory cytokine IL-10.

Figure 9A:
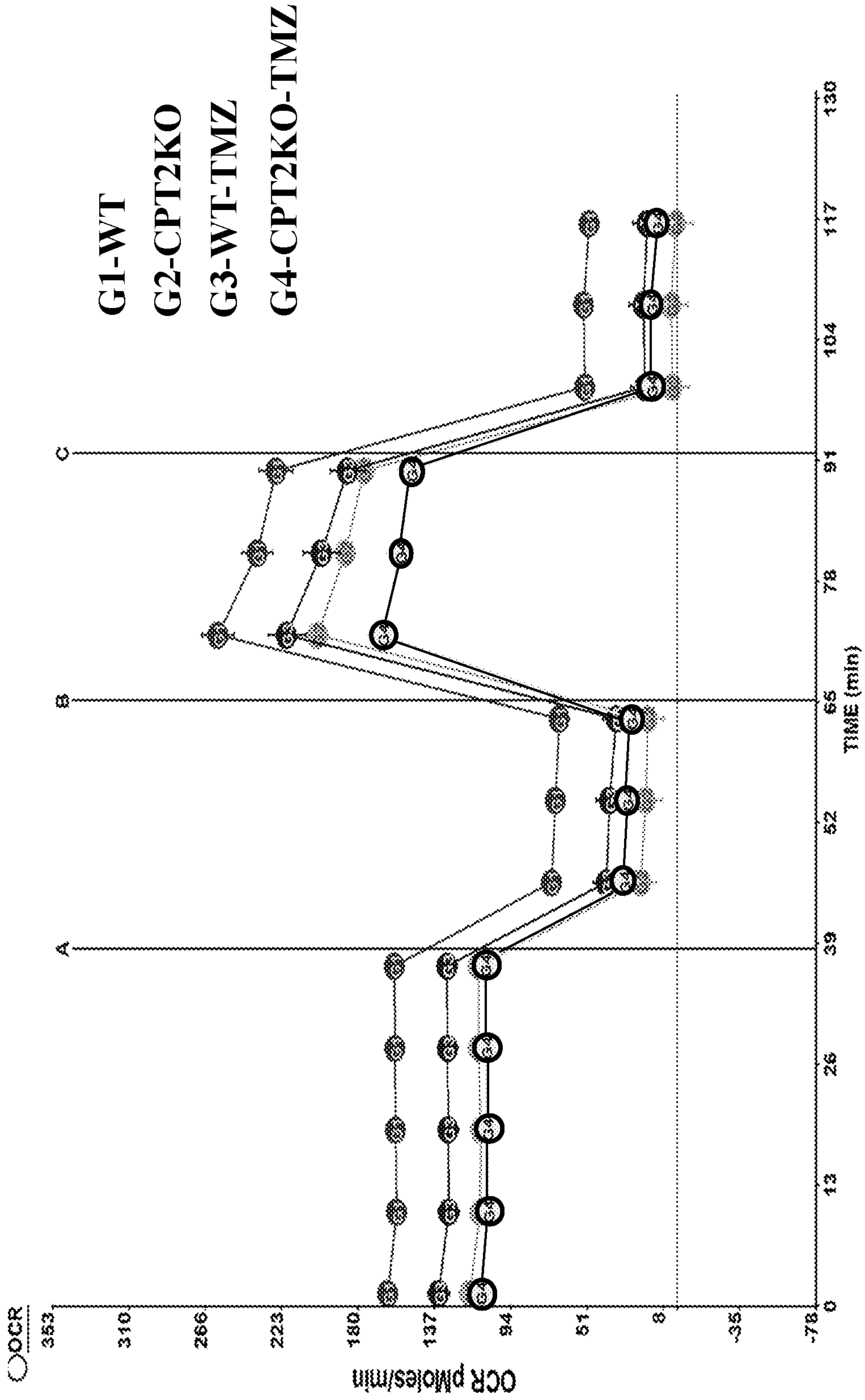
FIGS. 9A & 9B are graphs depicting reduction of OCR and E-CARD by host FAO inhibition. Wt and Cpt2 cKO BMDMs were treated with TMZ (5 nM) for 3 hours. OCR (FIG. 9A) and ECAR (FIG. 9B) were measured using SeaHorse metabolic flux assay. A=oligomycin, B=FCCP, and C=antimycin+rotenone. Data show average ±SEM from 16 replicates. In some cases the error bars were smaller than the data symbol.
Figure 9B:
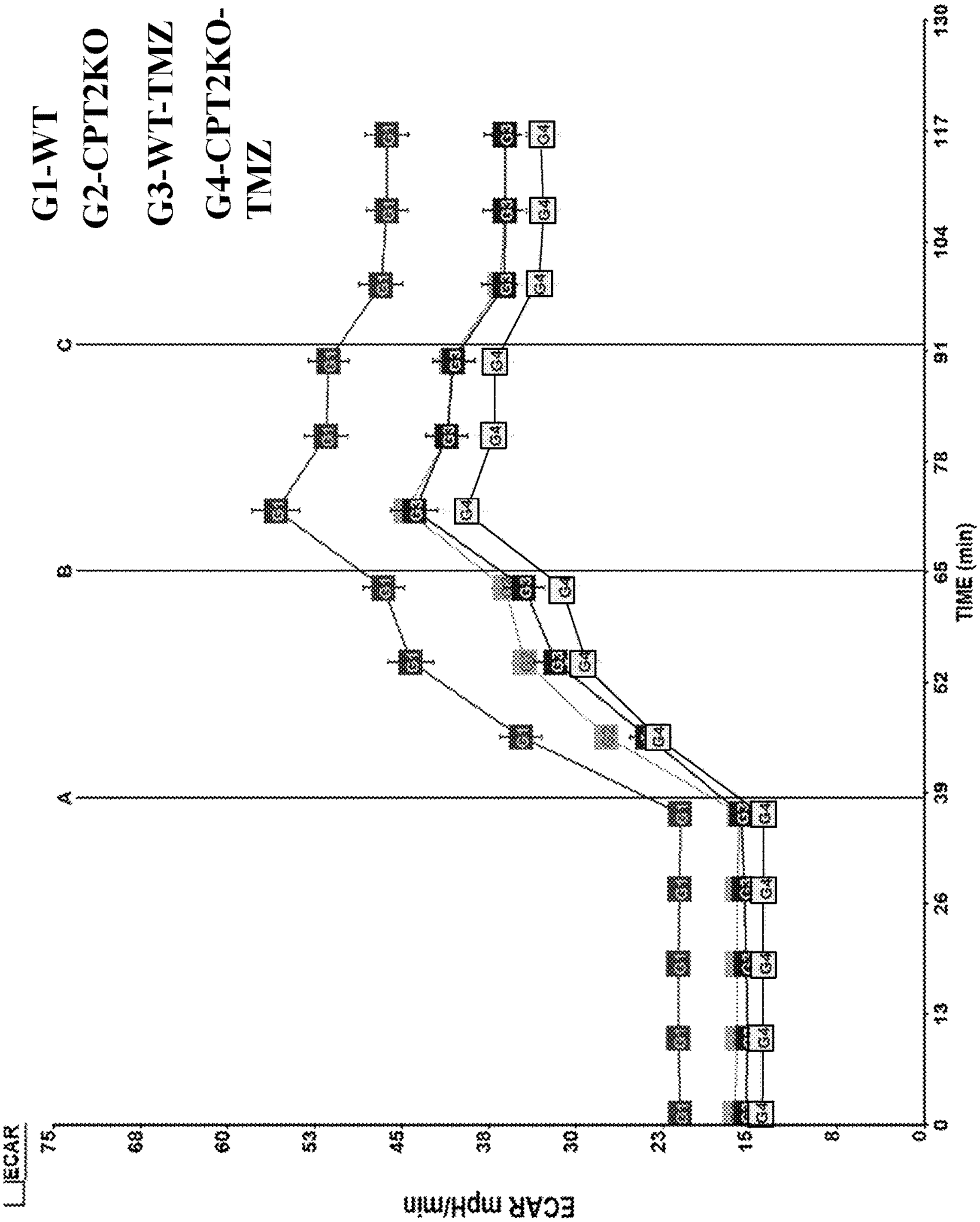

As shown in FIG. 9A, Cpt2 cKO and wild type macrophages had significantly reduced OCR as compared to wild type controls. Further, OCR of Cpt2 cKO BMDMs was comparable to wild type BMDMs treated with TMZ. A decrease in ECAR in wild type BMDMs was observed upon TMZ treatment, which was comparable to ECAR in Cpt2 cKO macrophages (FIG. 9B). Treatment of Cpt2 cKO BMDMs with TMZ did not further decrease the ECAR.

Next, the levels of various cytokines was determined in supernatants of uninfected and H37Rv infected wild type BMDMs at 24 and 72 hpi. No significant difference in levels of IL-6, TNF-α, IL-1α/β, and IL-10 with TMZ treatment was observed. No difference in expression of pro- and anti-inflammatory cytokines was detected in Mtb infected wild type as compared to Cpt2 cKO BMDMs, nor were there differences in response to TMZ treatment as determined by RNA-Seq.

Example 7

In this Example, efficacy of FAO inhibitors was determined in a mouse model of TB.

Figure 10:
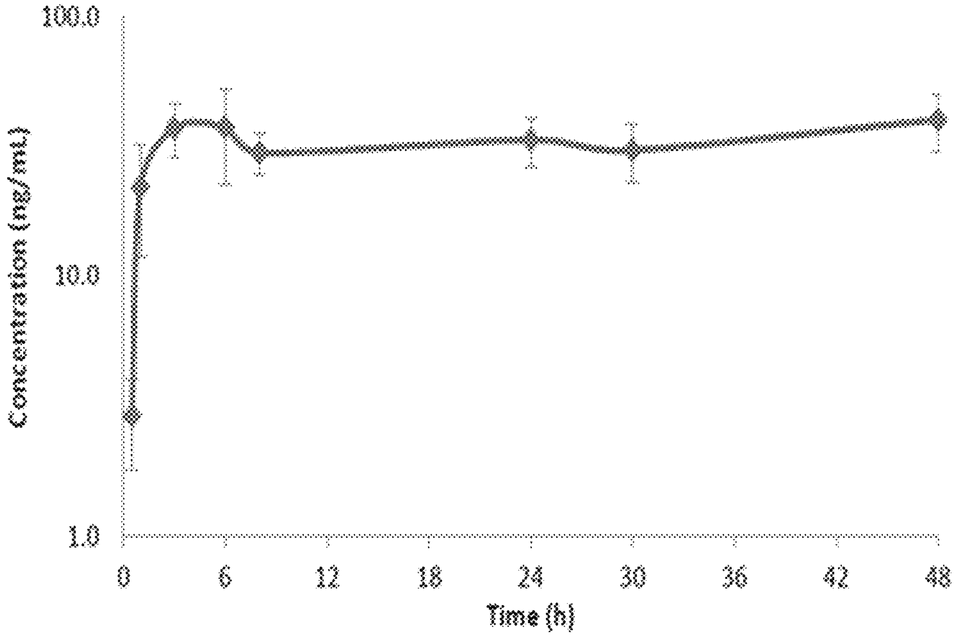
FIG. 10 depicts the pharmacokinetic profile of TMZ following a subcutaneous infusion of 10.66 mg/kg/day in female C57Bl/6 mice.

A pharmacokinetics (PK) study of TMZ in C57BL/6 mice was performed. TMZ had a half-life of less than an hour in mice after a single dose of TMZ was administered intravenously or orally (data not shown). Therefore, subcutaneous osmotic pumps were used to maintain steady state plasma levels of TMZ. A second PK study was performed using subcutaneous osmotic pumps (Alzet Osmotic Pumps) to establish the optimal infusion rate and dosing for a subsequent efficacy study. TMZ steady state exposure in mice was successfully achieved with the use of subcutaneous osmotic pumps. Administering a dose of 10.66 mg/kg/day achieved a steady state concentration of 31.3 ng/ml (FIG. 10).

Example 8

In this Example, efficacy of TMZ was determined in acute TB infection in mice.

Alzet osmotic pumps were implanted in C57B116 mice (8-10 weeks old) for delivering saline and TMZ at 1.68 mg/kg/day and 16.8 mg/kg/day, over a span of 2 weeks. 8 animals per group were used, which will allow for detecting a half-log difference between groups with at type I error of 5% and a power of 90%. Mice were infected with H37Rv by aerosol. Two mice were euthanized the next day to verify the infectious dose. Mtb CFU was estimated in lungs and spleen 2 weeks post infection.

Figure 11A:
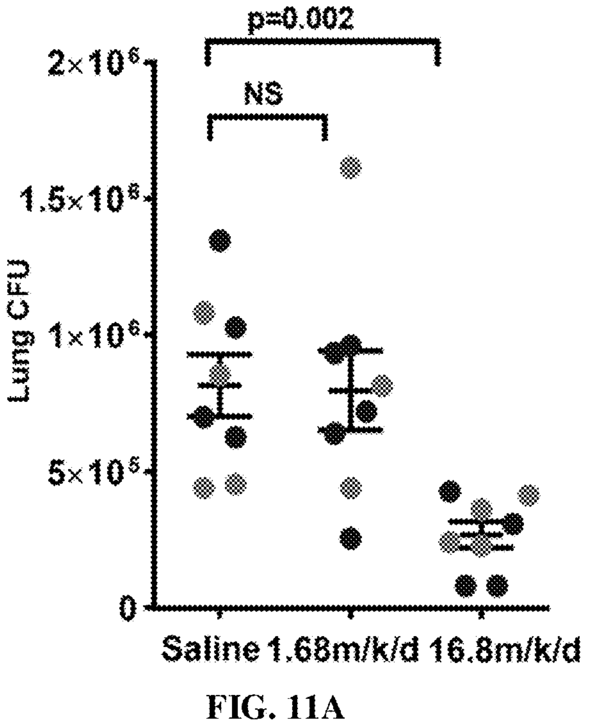
FIGS. 11A & 11B depict the efficacy of TMZ in Mtb infected mice. C57Bl/6 mice were infected with H37Rv and treated with TMZ for 2 weeks at indicated dose. H37Rv CFU are shown for lungs (FIG. 11A) and spleen (FIG. 11B). Light dots represent female mice; dark dots represent male mice. (m/k/d=mg/kg/day dose). P-value calculated using Mann-Whitney test.
Figure 11B:
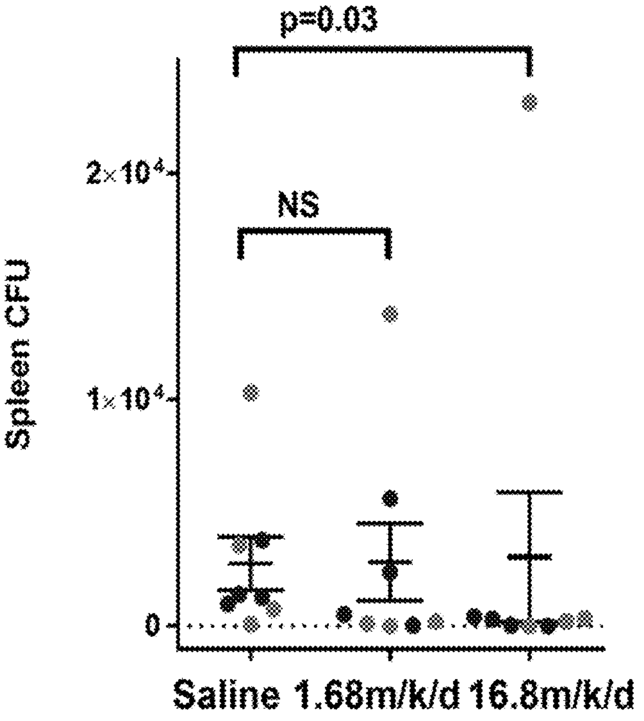

Aerosol challenge with H37Rv deposited ~1000 bacilli per mouse. This was considered a high pathogen burden. As shown in FIG. 11, mice administered TMZ at 16.8 mg/kg/day had significantly reduced bacterial burden in their lung and spleen tissues as compared to untreated control mice, leading to a 50-70% reduction in Mtb CFUs in the lungs with TMZ treatment.

The results of the in vivo TMZ efficacy study indicated that TMZ significantly reduced bacterial burden in acutely infected mice. The highest dose tested in mice (16.8 mg/kg/d) was predicted to achieve 135 nM free drug concentrations, whereas the 20 mg three times daily in humans achieves Cmax of 313 nM, and there is a wide therapeutic index. The results demonstrate that FAO inhibition induced an early ROS burst from the mitochondria and subsequently promoted xenophagy and NADPH oxidase activity. Induction of these host antimicrobial pathways restricted Mtb infection. Moreover, TMZ treatment reduced infectious burden in Mtb infected mice. Since TMZ has a favorable safety profile, it can rapidly advance to clinical trials.

Example 9

In this Example, the efficacy of FAO inhibitors against *Mycobacterium abscessus* was determined.

Figure 12A:
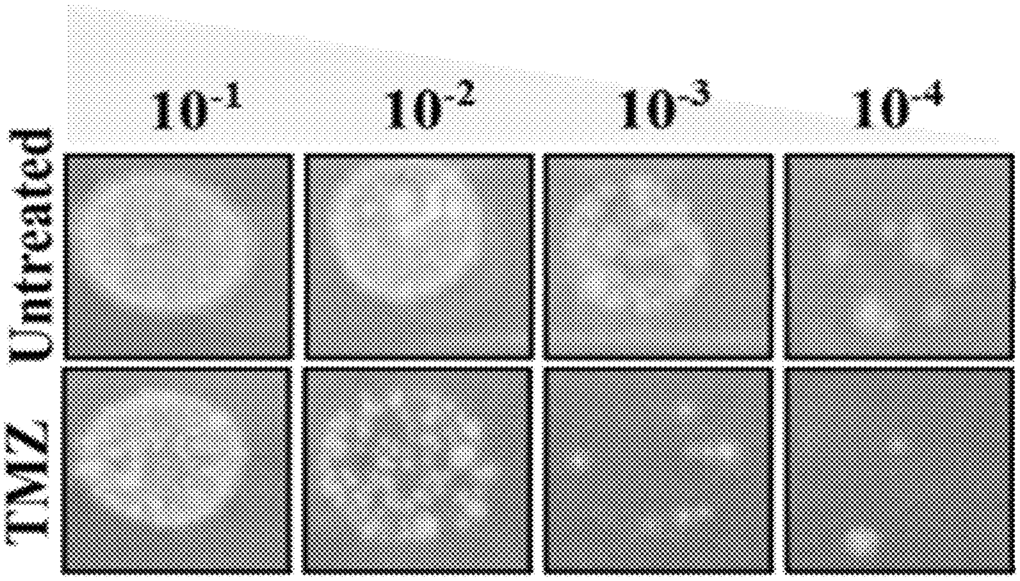
FIGS. 12A-12C depict macrophage FAO inhibition restriction of intracellular growth of *M. abscessus*. Pathogen burden was enumerated in RAW264.7 cells treated with TMZ 500 nM for 24 (FIG. 12A) and 48 hpi (FIG. 12B). Equal volumes of serial dilutions of infected macrophage lysates were spotted on 7H11 agar plates.
Figure 12B:
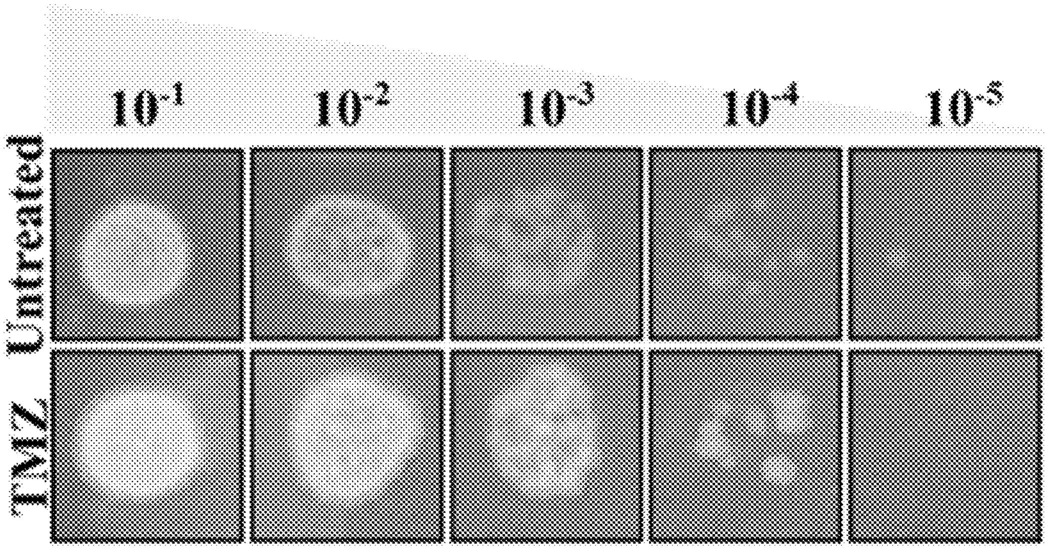
Figure 12C:
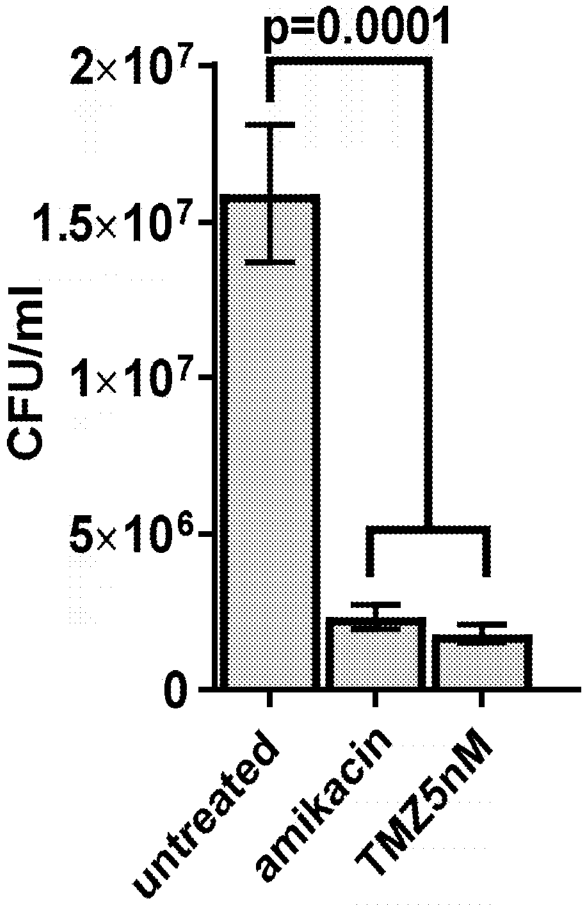

To determine whether the antimicrobial activity of FAO inhibition was specific for *M. tuberculosis*, TMZ was tested for its efficacy against the rapidly growing species, *M. abscessus*. RAW264.7 cells or wild type (wt) BMDMs were infected with *M. abscessus* at a multiplicity of infection (MOI) of 1:5. After 3 hours, the samples were washed three times daily with warm PBS and treated with amikacin (200 µg/ml) to remove the extracellular bacteria. 2 hours later, the samples were washed and maintained in culture medium supplemented with 500 nM TMZ. In parallel, amikacin was added as positive control. *M. abscessus* CFUs were estimated by plating macrophage lysates on 7H11 agar. As shown in FIGS. 12A-12C, TMZ treatment significantly decreased infection in both RAW264.7 cells and wt BMDMs. We conclude that the antimicrobial activity associated with FAO inhibition is not restricted to *M. tuberculosis*, but also works against rapid growing *M. abscessus.*

Example 10

In this Example, whether FAO inhibition perturbed electron flow within electron transport chain (ETC) resulting in ROS generation was determined.

Figure 14:
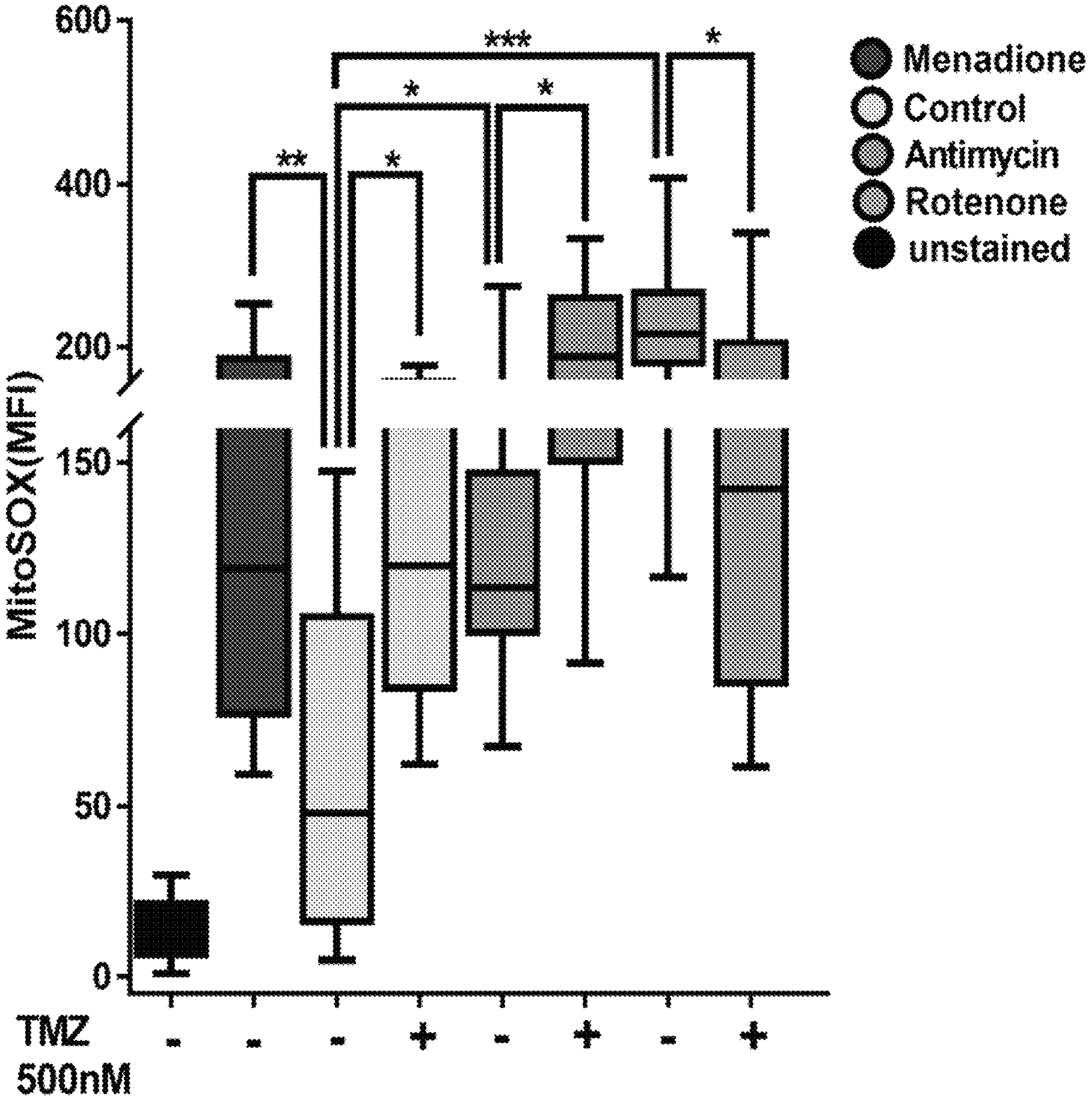
FIG. 14 depicts mitochondrial ROS production by TMZ requires ETC.

Mitochondrial ROS production was measured in macrophages treated with TMZ in combination with ETC inhibitors antimycin and rotenone. Rotenone inhibits Complex I (NADH coenzymeQ reductase) and antimycin is an inhibitor of Complex III (coenzyme Q: cytochrome C oxidoreductase). Uninfected BMDMs were treated with 500 nM TMZ for 3 hours. Thirty minutes prior to termination of the experiment, antimycin (30 µM) and rotenone (10 µM) were added. Menadione (60 µM, 30 mins), which causes mitochondrial depolarization, was used as a positive control. Mitochondrial ROS production was increased in samples treated with TMZ, antimycin and rotenone (FIG. 14A). However, contrasting results were observed when TMZ was used in combination with the ETC inhibitors. Combined treatment with TMZ and antimycin, enhanced ROS significantly more than individual treatment. Interestingly, ROS generated due to complex I inhibition was decreased in presence of TMZ. These results indicated that complex I was required by TMZ to induce mitochondrial ROS.

What is claimed is:

1. A method of treating a Mycobacteria infection in a subject in need thereof, the method comprising administering a dosage of trimetazidine to the subject to achieve a concentration ranging from about 1 nM to about 500 nM to reduce fatty acid oxidation by inhibiting 3-ketoacyl-CoA thiolase.

2. The method as set forth in claim 1, wherein the subject in need thereof has or is suspected of having *Mycobacterium tuberculosis* (Mtb), multidrug-resistant tuberculosis (MDR-TB), extensively drug-resistant tuberculosis (XDR-TB), *Mycobacterium abscessus, Mycobacterium fortuitum*, and *Mycobacterium* chelonae.

3. The method as set forth in claim 1 further comprising administering the trimetazidine in combination with at least one additional antimycobacterial agent.

4. The method as set forth in claim 3, wherein the antimycobacterial agent is selected from the group consisting of isoniazid (INH), rifampin, ethambutol, pyrazinamide, streptomycin, amikacin, capreomycin, bedaquiline, delamanid, a fluoroquinolone, linezolid, ethionamide, prothinamide, cycloserine, terizidone, p-aminosalicylic acid, clofazamine, amoxicillin and clavulanate, thioacetozone, clarithromycin, and imipenem.

5. The method as set forth in claim 1 further comprising administering the trimetazidine in combination with at least one additional agent selected from the group consisting of metformin, statins, valproic acid, carbamezapine, vorinostat, phenylbutyrate, rapamycin, imatinib, desipramine, alisporivir, COX inhibitors, zileuton, bestatin, sildenafin, and pentyoxyfylline.

6. A method of inhibiting intracellular growth of Mtb in a subject in need thereof, the method comprising administering a dosage of trimetazidine to the subject to achieve a concentration ranging from about 1 nM to about 500 nM to reduce fatty acid oxidation by inhibiting 3-ketoacyl-CoA thiolase.

7. The method as set forth in claim 6, wherein the subject in need thereof has or is suspected of having *Mycobacterium tuberculosis* (Mtb), multidrug-resistant tuberculosis (MDR-TB), and extensively drug-resistant tuberculosis (XDR-TB).

8. The method as set forth in claim 6 further comprising administering the trimetazidine in combination with at least one additional antimycobacterial agent.

9. The method as set forth in claim 8, wherein the antimycobacterial agent is selected from the group consisting of isoniazid (INH), rifampin, ethambutol, pyrazinamide, streptomycin, amikacin, capreomycin, bedaquiline, delamanid, a fluoroquinolone, linezolid, ethionamide, prothinamide, cycloserine, terizidone, p-aminosalicylic acid, clofazamine, amoxicillin and clavulanate, thioacetozone, clarithromycin, and imipenem.

10. The method as set forth in claim 6 further comprising administering the trimetazidine in combination with at least one additional agent selected from the group consisting of metformin, statins, valproic acid, carbamezapine, vorinostat, phenylbutyrate, rapamycin, imatinib, desipramine, alisporivir, COX inhibitors, zileuton, bestatin, sildenafin, and pentyoxyfylline.

11. A method of inhibiting intracellular growth of *Mycobacterium abscessus* in a subject in need thereof, the method comprising administering a dosage of trimetazidine to the subject to achieve a concentration ranging from about 1 nM to about 500 nM to reduce fatty acid oxidation by inhibiting 3-ketoacyl-CoA thiolase.

12. The method as set forth in claim 11 further comprising administering the trimetazidine in combination with at least one additional antimycobacterial agent.

13. The method as set forth in claim 11 further comprising administering the trimetazidine in combination with at least one additional agent selected from the group consisting of metformin, statins, valproic acid, carbamezapine, vorinostat, phenylbutyrate, rapamycin, imatinib, desipramine, alisporivir, COX inhibitors, zileuton, bestatin, sildenafin, and pentyoxyfylline.

* * * * *